(12) United States Patent  (10) Patent No.: US 8,556,852 B2
Jayaraman  (45) Date of Patent: Oct. 15, 2013

(54) DELIVERY OF THERAPEUTIC SUBSTANCE AND MARKING SUBSTANCE THROUGH INTRA LUMEN EXPANSION OF A DELIVERY DEVICE

(76) Inventor: Swaminathan Jayaraman, Fremont, CA (US)

( * ) Notice: Subject to any disclaimer, the term of this patent is extended or adjusted under 35 U.S.C. 154(b) by 0 days.

(21) Appl. No.: 13/454,241

(22) Filed: Apr. 24, 2012

(65) Prior Publication Data

US 2012/0265067 A1  Oct. 18, 2012

Related U.S. Application Data

(63) Continuation of application No. 12/016,232, filed on Jan. 18, 2008, now Pat. No. 8,162,880.

(51) Int. Cl.
*A61M 31/00* (2006.01)
*A61M 37/00* (2006.01)

(52) U.S. Cl.
USPC ............................... 604/103.02; 604/103.06

(58) Field of Classification Search
USPC ............... 604/95.03, 103.02, 103.03, 103.06, 604/103.09, 101.01
See application file for complete search history.

(56) References Cited

U.S. PATENT DOCUMENTS

| | | | |
|---|---|---|---|
| 2010/0076401 A1* | 3/2010 | Von Oepen et al. | 604/509 |
| 2010/0179475 A1* | 7/2010 | Hoffmann et al. | 604/103.02 |
| 2011/0144578 A1* | 6/2011 | Pacetti et al. | 604/96.01 |
| 2012/0310210 A1* | 12/2012 | Campbell et al. | 604/509 |

* cited by examiner

*Primary Examiner* — Nicholas Lucchesi
*Assistant Examiner* — Rebecca E Eisenberg
(74) *Attorney, Agent, or Firm* — Fleit Gibbons Gutman Bongini & Bianco PL; Paul D. Bianco; Martin Fleit

(57) ABSTRACT

The invention provides a balloon catheter formed with a plurality of depressions. The balloon is coated with a matrix incorporating a therapeutic substance, which fills the depressions. When the balloon is expanded within a body lumen, the therapeutic substance may diffuse into the lumen wall, or all or a portion of the coating transfers to the lumen wall. A lattice frame may surround the balloon, applied prior to coating if the coating is to transfer, operative to maintain a more linear balloon profile during inflation, promoting more even transfer pressure. A contrast dye is incorporated into the transferred coating, enabling ready location and inspection of the treated lumen area.

20 Claims, 4 Drawing Sheets

DELIVERY OF THERAPEUTIC SUBSTANCE AND MARKING SUBSTANCE THROUGH INTRA LUMEN EXPANSION OF A DELIVERY DEVICE

CROSS REFERENCE TO RELATED APPLICATIONS

This application is a continuation of U.S. patent application Ser. No. 12/016,232, filed Jan. 18, 2008, now U.S. Pat. No. 8,162,880.

FIELD OF THE INVENTION

The present invention relates to balloon catheters for distal drug delivery within the body, wherein the balloon catheter applies a therapeutic substance to the interior surface of a body lumen upon inflation therein.

BACKGROUND OF THE INVENTION

The human body includes arterial and venous conduits which run throughout various sections of the human body. These conduits conduct blood into and from the heart which maintain the circulation that helps to sustain the metabolic events in the body. The vessels undergo biological, physiological, and mechanical changes depending on the body metabolism which determine the functionality of the wall of the artery.

Sometimes the wall of an artery becomes occluded due to deposits of fatty tissues which in turn form plaque on the walls of the artery. These plaques then have to be removed to restore the normal function of the artery. One known mechanism of removing the plaque is to compress the plaque against the wall of the artery using a balloon catheter. This procedure is called Percutaneous (under the skin) Transluminal (under x-ray guidance) Coronary (region of intervention) Angioplasty (plaque compression) or PTCA.

For a PTCA procedure to be accomplished, a balloon catheter and a guidewire along with a guiding catheter are typically required. The guiding catheter is normally introduced in a groin artery and pushed upwards towards the aorta until it reaches the mouth of the coronary artery. Once the guiding catheter is placed at the opening of the coronary artery, a highly floppy wire is introduced into the guiding catheter such that the wire crosses the mouth of the guiding catheter and goes into the coronary artery. It then has to reach the site of the lesion (plaque) which is usually a very tortuous route and the operator (the cardiologist) has to struggle to reach the guidewire in place. Once a guidewire has crossed the lesion, it is then pushed distally to the lesion so that it remains at a safe place. This is to ensure that the wire does not slip out of the lesion.

In addition to angioplasty, balloon catheters are used for balloon septostomy, wherein the balloon enlarges an opening in the heart for greater blood flow, and tuboplasty, wherein the balloon is used to correct a fallopian tube obstruction. Balloon catheters are further used to deliver stents, or round wire forms which are typically used to provide support to a blood vessel, and for installing filters, to prevent migration of blood clots in the treatment of thrombophlebitis.

Frequently, it may be advantageous to deliver a substance which helps to address the core problem, aid in healing, or prevent recurrence of the problem. This is addressed, for example, in U.S. Pat. No. 5,810,767 to Klein, wherein a balloon is provided with pockets which, when the balloon is inflated, are filled with a liquid therapeutic substance. The objective in Klein is to maintain the balloon in contact with the body lumen, whereby the liquid is maintained within the pockets against the body lumen as it is infused, and is not quickly swept away with blood flow. In this manner, treatment to the body lumen may be maintained while the balloon is inflated.

In Klein, however, the application of a therapeutic substance only takes place while the balloon is inflated. To maintain blood flow, the balloon must be repeatedly deflated for a period of time, then reinflated to resume treatment. Thus, the period of treatment is thus necessarily short, and terminates once the surgical procedure is over, and the catheter is removed.

Another approach to delivering a therapeutic substance may be found in U.S. Pat. No. 7,055,237 to Thomas. Thomas does not disclose the advantages of delivering a substance using a balloon catheter itself as the delivery device. Rather, the reference discloses a stent as the delivery device, the stent itself being delivered by catheter. In Thomas, the stent is fabricated with a series of indentations or dimples in the surface of the stent, which act to increase the amount of drug the stent can be coated with. In use, the stent is expanded against the vessel wall, whereupon the drug is released.

In Thomas, drug is delivered only while the stent remains in the body. Where it is intended for the stent to remain in the body for an extended period, the delivery time period may be adequate. Where it is not necessary to leave an implant in the body, however, Thomas fails to provide a solution.

In U.S. Pat. No. 6,364,856 to Ding et al., however, a balloon catheter as well as a stent is used to deliver a biologically active material or drug to a lumen wall. In Ding, a non-hydrogel sponge having a plurality of voids is formed around the balloon. A non-hydrophilic substance to be delivered is incorporated into the sponge. As the balloon is inflated, the non-hydrophilic substance is squeezed out of the sponge, where it diffuses into contacting tissue. Again, however, delivery is effectively halted when the balloon is removed. In addition, as in the previous references, once the balloon has been withdrawn, the radiopaque marker within or near the balloon which identifies the location of the treatment site is also removed.

In U.S. Pat. No. 5,102,402 to Dror et al., a balloon catheter has a coating containing microcapsules, whereby the coating may be released from the balloon onto the lumen, and where the microcapsules are crushed during inflation, releasing their contents. A radiopaque compound may be incorporated into the microcapsules, whereby the vessel may be visualized by fluoroscopy or similar methods.

In Dror, however, even if a coating is transferred to the lumen wall, all of the crushed microcapsules release their contents at once, where much of the therapeutic or radiopaque substance may be washed away by the flow of materials within the lumen.

There remains, therefore, a need to prolong the application of the therapeutic substance at the treatment site, while maintaining radiopaque marking.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 CFR §1.56(a) exists.

SUMMARY OF THE INVENTION

In accordance with the invention, a balloon catheter is provided for delivering a therapeutic substance to a body lumen. A balloon catheter is formed with a plurality of depressions, wells or reservoirs, into which a therapeutic substance is placed. When the balloon is expanded within a body lumen, the therapeutic substance may infuse, diffuse, elute, or physically transfer to the lumen wall.

In another embodiment of the invention, a balloon catheter surface is roughened, or formed with a series of undulations, which may similarly form a reservoir for containment of a therapeutic substance.

In an additional embodiment of the invention, a balloon catheter has surface reservoirs and outer surface coated with a therapeutic substance. In this manner, the therapeutic substance is transferred to the vessel wall upon inflation, and additional therapeutic substance is wicked from the reservoirs through the remainder of the coating, to the vessel walls.

Accordingly, a larger quantity of therapeutic substance may be delivered, without a requirement of infusion, and without leaving an implant within the body.

In a further embodiment of the invention, a balloon catheter is provided with two coatings. One coating comprises a therapeutic substance, and another is a coating of contrast agent, operative to mark a site of therapeutic substance administration for future examination and evaluation. The contrast agent may alternatively be incorporated into a matrix with the therapeutic substance. Accordingly, there is no disadvantage to removing an implant or device incorporating a radiopaque marker from the body, with respect to tracking the location of interest, since a marker incorporated into the coating is now associated with the lumen wall.

In a further embodiment of the invention, a balloon catheter is provided with projections operative to engage the body lumen and facilitate migration of the therapeutic substance from the balloon surface into the intima, media, or adventitia of a blood vessel.

Accordingly, the amount of therapeutic substance which must be delivered can be reduced, since the substance is delivered directly to an area of the lumen wall most directly benefiting from treatment.

A catheter in accordance with the invention may be inserted within the body and guided by a guide wire, and may be provided with means to maintain blood flow while inflated, including, for example, the use of one or more infusion ports in the catheter body.

A balloon catheter is covered with coatings as described herein in either the inflated or deflated state, by any of a wide variety of known means. In accordance with an aspect of the invention, however, the reservoirs formed on the balloon surface are filled by micropipette, particularly where the therapeutic substance to be administered is only readily available in very small quantities. This may include, for example, genetically modified materials.

In yet another embodiment in accordance with the invention, a coating is provided with a release coating that weakly adheres to the balloon, and a transfer coating that bonds with greater strength to the lumen wall. In this manner, the coating is transferred to the lumen upon inflation, and remains in place after the balloon is deflated. To aid in positioning the catheter, the transfer coating may be provided with a lubricious coating which dissolves, disintegrates or biodegrades within a desired time frame, wherein the transfer coating is exposed once the balloon is in place. Alternatively, the balloon may be encased within a sheath which is mechanically removed at the appropriate time.

Accordingly, a balloon catheter does not need to remain in place throughout the time of administration of the therapeutic substance. Similarly, the need to implant a stent or other device, and leave it in the body following surgery, may be avoided.

In another aspect of the invention, one or more coatings are formed with sufficient thickness and resilience to form a protective cushion, in order to reduce tissue damage during inflation, or during catheter placement. The cushion may be an eluting coating, or may be a coating which transfers to the vessel wall.

A balloon catheter has a tendency to inflate to a larger diameter at a central, less supported area than at the peripheral points of attachment. This results in a greater transfer pressure near this central, or middle area of the balloon, than at the balloon ends. For optimal transfer, it is desired to have a uniform pressure of engagement across the entire area of balloon/lumen contact.

Thus, in accordance with a further aspect of the invention, a lattice comprising for example a mesh or woven lattice frame is provided, operative to encourage a uniform contact pressure of the balloon surface against the lumen wall. The frame may be installed onto the balloon when deflated or inflated, but in accordance with the invention, is resilient, whereby when the balloon is deflated, the wire frame shrinks to maintain conforming contact with the balloon. In this manner, the wire frame is removed with the balloon at the conclusion of the procedure.

As the wire frame is removed with the catheter, it may be advantageous to apply any coatings to be transferred to the lumen above the wire frame. However, since the wire presents a meshed surface, therapeutic substance within reservoirs, or in coatings beneath the frame, may still diffuse into the lumen wall if the frame is installed above one or more coatings.

The wire frame described is additionally beneficial for promoting a uniform contact pressure for coatings containing substances which must diffuse or elute into the lumen while the balloon is expanded, as well. In this application, an even contact pressure increases the likelihood of consistent dosing throughout the region of desired application.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

In the description which follows, any reference to direction or orientation is intended primarily and solely for purposes of illustration and is not intended in any way as a limitation to the scope of the present invention. Also, the particular embodiments described herein, although being preferred, are not to be considered as limiting of the present invention.

Figure 1:
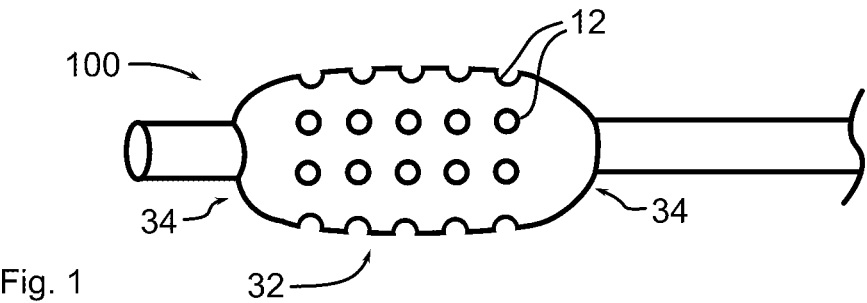
FIG. 1 illustrates an inflated balloon catheter in accordance with the present invention.

Referring now to the figures in which like reference numerals refer to like elements, an exemplary balloon catheter 100 in accordance with the invention is illustrated in FIG. 1. Balloon 100 is formed with a plurality of depressions, wells or reservoirs 12, into which a therapeutic substance is placed. When the balloon is expanded within a body lumen 200, the therapeutic substance may infuse, diffuse, elute, or physically transfer to the lumen wall. In the illustration, large reservoirs 12 are shown for clarity. In practice, reservoirs 12 may be significantly smaller and more numerous.

Balloons are typically made of compliant, semi-compliant or a non-compliant polymeric material, or a combination of a polymeric material. Materials include but are not limited to polyethylene terephthalate (PET), polyethylene (PE), nylon, blends and copolymers of nylon, polyether block amides, and polyurethane. In use, the balloon can be inflated with a gas, or saline or a contrast fluid as is known by those skilled in the art. High pressure balloons may additionally be used and fabricated in accordance with the invention.

To fabricate balloon 100, as well as other balloons in accordance with the invention, methods known in the art may be used for molding, casting, stamping, or otherwise producing bumps, indentations, undulations, peaks, points, wells or reservoirs in the rubber or plastic balloon material precursor, which is later formed into the balloon. Alternatively, a stamp, die or other means may be applied to the fabricated balloon, possibly including the application of heat, and or a mandrel.

A therapeutic substance in accordance with the invention is any material that has an affect on the subject lumen, and includes substances which have a therapeutic affect, or are used for a pedagogic or diagnostic purpose. Certain of these are described in my U.S. patent application Ser. No. 10/696,174, incorporated herein by reference in its entirety.

One common objective to applying the therapeutic coating is to either mediate or suppress a tissue response at the site of implantation. For example in intravascular situations, one common outcome of implanting a foreign body is for an intense reaction at the site of implantation. This intense reaction can result from either the implantation itself or the stresses generated after implantation. Due to the reaction, there is an obvious interaction by the vessel wall to compensate for this injury by producing a host of tissue related responses that is generally called "healing due to injury." It is this healing process that the therapeutic coating attempts to mediate, suppress, or lessen. In some instances, this healing process is excessive in which it occludes the entire lumen providing for no blood flow in the vessel. This reoccluded vessel is also called a restenotic vessel.

According to the present invention, a coating for an intravascular implant is provided. The coating can be applied either alone, or within a polymeric matrix, which can be biostable or bioabsorbable, to the surface of an intravascular device. The coating can be applied directly to the balloon, or on top of a polymeric substrate, i.e. a primer. If desired, a top coat can be applied to the therapeutic coating.

The intravascular implant coating according to the present invention comprises a therapeutically effective amount of a first agent, and optionally a therapeutically effective amount a second agent, or additional agents.

Examples include an agent acting on a calcium independent cellular pathway, or a calcium dependent cellular pathway, to treat for example, hyperproliferative vascular disease. In an exemplary embodiment, the first agent is rapamycin and the second agent is cyclosporine A.

Alternatively, the therapeutic intravascular implant coating includes an effective amount of at least one therapeutic agent to treat or prevent a disease process of a vascular disease of a patient, wherein the effective amount of at least one therapeutic agent cures the vascular disease.

The foregoing is merely illustrative, and the invention is not limited to any particular therapeutic treatment. Additional examples include macrolide immunosuppressants, anti-inflammatory agents, non-proliferative agents, anti-coagulants, anti-platelet agents, Tyrosine Kinase inhibitors, anti-infective agents, anti-tumor agents, anti-leukemic agents, or combinations thereof.

Therapeutic coatings can behave in different ways. For example, depending upon the kind of therapeutic agent used, the various cellular levels of mechanisms are tackled. Some of the therapeutic agents act on the growth factors that are generated at the site of implantation or intervention of the vessel. Some other therapeutic agents act on the tissues and suppress the proliferative response of the tissues. Others act on the collagen matrix that comprises the bulk of the smooth muscle cells.

A key benefit to administering a therapeutic substance by direct application to a treatment site is the avoidance of systemic administration, which subjects the entire body to the therapeutic substance, which is often disadvantageous. In accordance with the invention, application of the therapeutic substance is targeted to the tissues affected, and the local dose may be quite high without causing harm to other areas of the body.

Figure 2:
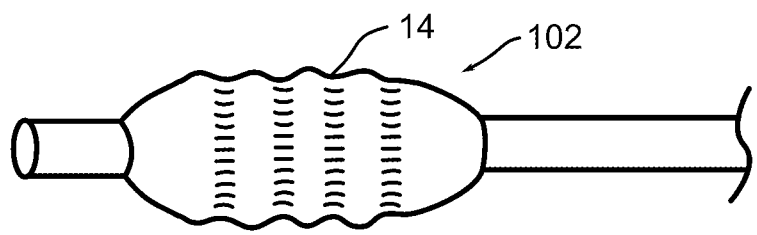
FIG. 2 illustrates an alternative balloon catheter, in accordance with the invention.

Referring now to FIG. 2, in another embodiment of the invention, a balloon catheter 102 surface is roughened, or formed with a series of undulations 14, which may similarly form a reservoir for containment of a therapeutic substance, as described for balloon 100. Undulations 14 may be fabricated as described with respect to balloon 100.

In an additional embodiment of the invention, a balloon catheter 100 has surface reservoirs 12 and outer surface coated with a therapeutic substance 16. In this manner, the therapeutic substance is transferred to the vessel wall 200 upon inflation, and additional therapeutic substance is wicked from the reservoirs through the remainder of the coating, to the vessel wall.

Accordingly, a larger quantity of therapeutic substance may be delivered, without a requirement of infusion, and without leaving an implant within the body.

In a further embodiment of the invention, a balloon catheter is provided with two coatings 16,18. In one embodiment, one coating comprises a therapeutic substance, and another a coating of dye or radiopaque contrast agent, operative to mark a site of therapeutic substance administration to be readily viewable for future examination and evaluation using any of a variety of medical imaging apparatus, as is known in the art. The contrast agent may alternatively be incorporated into a coating containing therapeutic substance. An advantage is thereby obtained, whereby the site treated by the transferred coating remains marked after the catheter and balloon are removed.

Whether provided as a separate coating, or admixed into another coating, the presence of a contrast agent within the transferred coating presents the advantage of marking the site of therapy, and thus overcomes the disadvantage of removing an implant or device having a radiopaque marker from the body, whereby tracking the location of interest and treatment is rendered more difficult.

Figure 3:
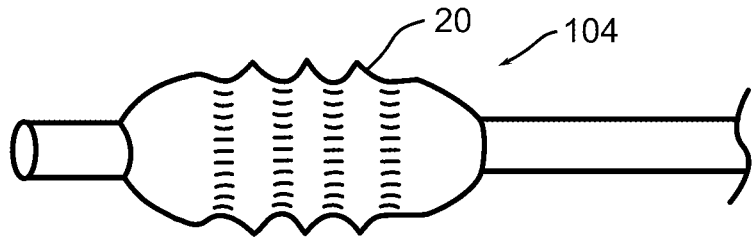
FIG. 3 illustrates a further alternative of a balloon catheter, in accordance with the invention.
Figure 4:
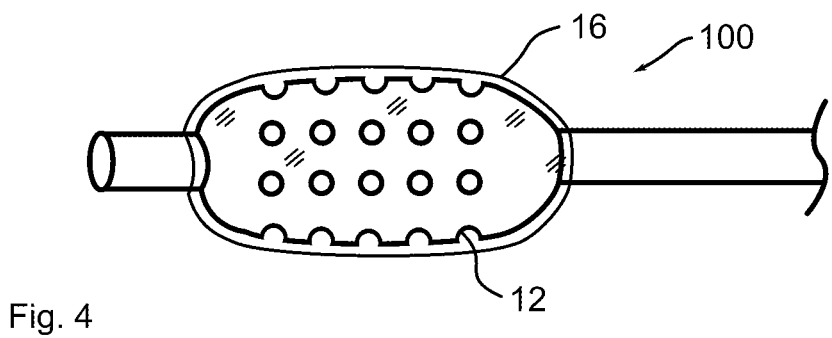
FIG. 4 illustrates the balloon catheter of FIG. 1, with a coating in accordance with the invention.
Figure 5:
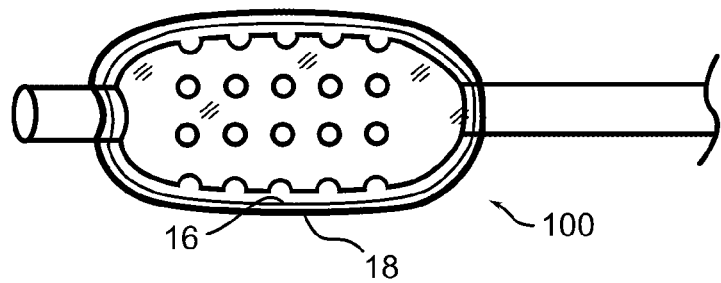
FIG. 5 illustrates the balloon catheter of FIG. 1, with an additional coating in accordance with the invention.
Figure 6:
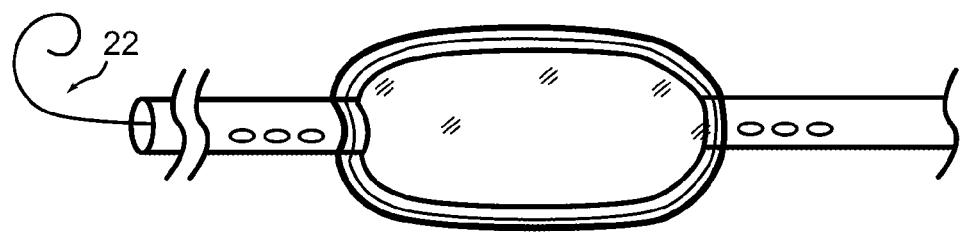
FIG. 6 illustrates a coated perfusion balloon catheter in accordance with the invention, with an installed guidewire.
Figure 7:
FIG. 7 illustrates the balloon catheter of FIG. 6, deflated.
Figure 8:
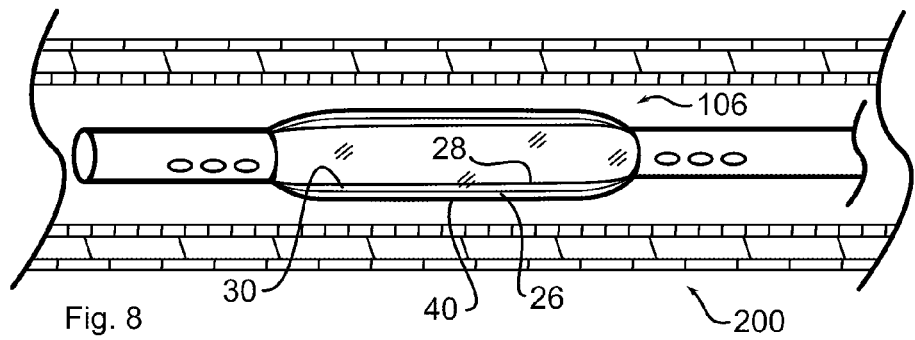
FIG. 8 illustrates the balloon catheter of FIG. 7, disposed within a body lumen.
Figure 9:
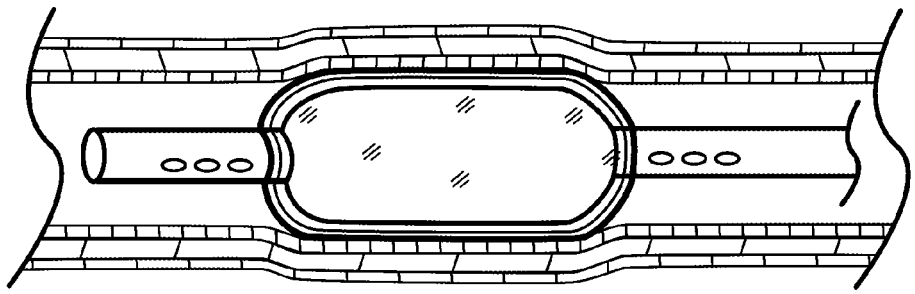
FIG. 9 illustrates the balloon catheter of FIG. 8, inflated within a body lumen.

In a further embodiment of the invention, with reference to FIG. 3, a balloon catheter 104 is provided with projections 20 operative to engage the body lumen and facilitate migration of the therapeutic substance from the balloon surface into the intima, media, or adventitia of a blood vessel. Accordingly, the amount of therapeutic substance which must be delivered can be reduced, since the substance is delivered directly to an area of the lumen wall most directly benefiting from treatment. Projections 20 are shown enlarged for clarity, however in practice they may be considerably smaller and more numerous, corresponding to the thickness of the intima or intima and media layers combined of a blood vessel. In one embodiment, projections 20 pierce the underlying layer, exposing the target layer to the therapeutic substance. In another embodiment, projections 20 urge the therapeutic substance into the interstices between cells, or interstitial space, speeding delivery of the therapeutic substance into the target layer.

A catheter in accordance with the invention may be inserted within the body and guided by a guide wire 22, and may be provided with means to maintain blood flow while inflated, including, for example, through the use of one or more perfusion ports 24 in the catheter body. As known in the art, a lumen (not shown) within the catheter is provided for inflating the balloon, which is not communicative with a lumen or passage past the balloon for blood flow through the perfusion ports.

A balloon catheter is covered with coatings as described herein in either the inflated or deflated state, by any of a wide variety of means, including spraying, such as by atomizing nozzle or ultrasonic sprayer, coating, and dipping. In accordance with an aspect of the invention, however, the reservoirs formed on the balloon surface are filled by micropipette, particularly where the therapeutic substance to be administered is only readily available in very small quantities. Pressurized substance may also be sprayed from a micropipette. Coatings may be applied at any point in time, from the original manufacture of the balloon, to a point just before insertion.

Figure 10:
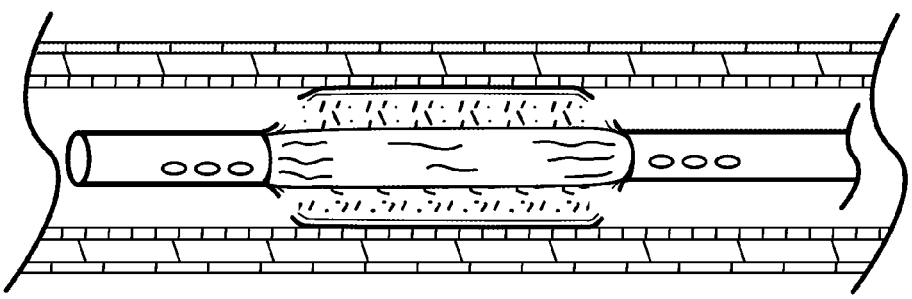
FIG. 10 illustrates the balloon catheter of FIG. 9, deflated, after substance delivery.
Figure 11:
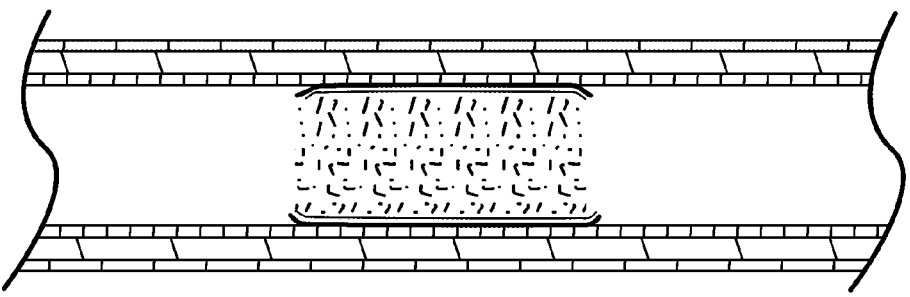
FIG. 11 illustrates the lumen depicted in FIG. 10, coated with substance delivered.

With reference to FIGS. 8-11, in yet another embodiment in accordance with the invention, balloon 106 is provided with a release coating 28 that weakly adheres to balloon 106, and an outermost transfer coating 40, which bonds with greater strength to the lumen wall than does release coating 28 to balloon 106. Alternatively, release coating 28 may be positioned between any two coatings, in accordance with the invention. In this manner, at least one coating is transferred to the lumen upon inflation, as in FIG. 9, and remains in place after the balloon is deflated, as can be seen in FIGS. 10 and 11.

To aid in positioning the catheter, the transfer coating may be provided with a lubricious coating which dissolves, disintegrates or biodegrades within a desired time frame, wherein the transfer coating is exposed once the balloon is in place. Alternatively, the balloon may be encased within a sheath which is mechanically removed at the appropriate time, using techniques known in the art.

Accordingly, a balloon catheter does not need to remain in place throughout the time of administration of the therapeutic substance. Similarly, the need to implant a stent or other device, and leave it in the body following surgery, may be avoided.

In another aspect of the invention, one or more coatings, such as coatings 26 or 30, or a separate coating, is formed with sufficient thickness and resilience to form a protective cushion, in order to reduce tissue damage during catheter placement, during inflation, and while the balloon remains inflated. The cushion coating may comprise any resilient biocompatible material, including gels, hydrogels, or a polymeric substance. The cushion may be an eluting coating, or may be a coating which transfers to the vessel wall.

Referring again to FIGS. 1-4, a balloon catheter has a tendency to inflate to a larger diameter at a central, less supported area 32 than at the peripheral points of attachment 34. This results in a greater transfer pressure near this central, or middle area of the balloon, than at the balloon ends, during and after inflation. For optimal transfer of at least one coating to the lumen, or for even diffusion of a therapeutic substance from a coating to the lumen, it is desired to have a uniform pressure of engagement across the entire area of balloon/lumen contact.

Figure 12:
FIG. 12 illustrates a wire mesh in accordance with the invention.
Figure 13:
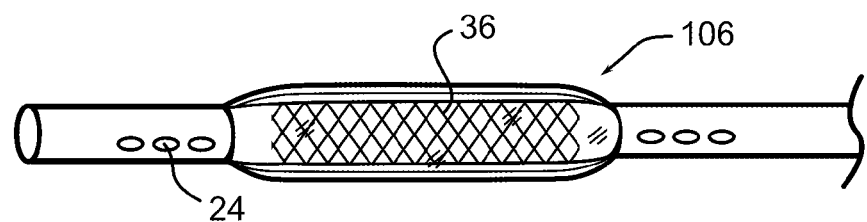
FIG. 13 illustrates the wire mesh of FIG. 12, disposed about the deflated balloon catheter of FIG. 7.
Figure 14:
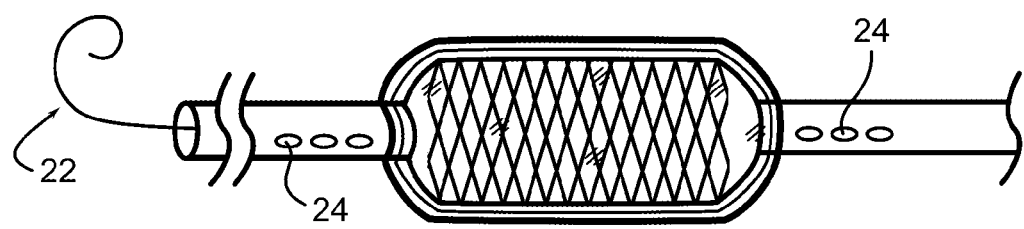
FIG. 14 illustrates the balloon catheter and wire mesh of FIG. 13, inflated.

Thus, in accordance with a further aspect of the invention, and with reference to FIGS. 12-14, a mesh or woven lattice frame 36 is provided, operative to encourage a uniform surface expansion and thus uniform contact pressure of the balloon surface against the lumen wall. A balloon is weakest at points furthest from an attachment point, and therefore stretches outwards forming its greatest diameter near the center of the balloon. Frame 36, being a lattice structure, requires a generally equal pressure throughout its length to expand. If frame 36 is significantly stiffer than balloon 100, for example, the weakness of the balloon center is supported by the frame, and is allowed to bulge to a lesser extent. Frame 36 may additionally be constructed to have stiffer segments 38 towards the center of frame 36, to further encourage uniform expansion, and thus a more linear inflated profile, of an assembled balloon and frame.

The wire frame may be installed onto the balloon when deflated or inflated, but in accordance with the invention, is resilient, whereby when the balloon is deflated after inflation, the wire frame shrinks to maintain conforming contact with the balloon. In this manner, the wire frame is removed with the balloon at the conclusion of the procedure.

Frame 36 is conveniently fabricated from wires, however flat strips or other elongated forms are additionally contemplated. Frame 36 encircles a balloon as described herein, in the manner of a sleeve. Frame 36 is disposed about the deflated catheter body and one or more coatings are applied above frame 36 as described above. As the wire frame, in accordance with one embodiment of the invention, is removed with the catheter, it is advantageous to apply any coatings to be transferred to the lumen above the wire frame. However, since the wire presents a open mesh or weave surface, therapeutic substance within reservoirs, or in coatings beneath the frame, may still diffuse into the lumen wall if frame 36 is installed above one or more coatings.

In one embodiment, frame 36 is installed onto deflated balloon 106, where it remains in place due to frictional engagement due to resilience of frame 36, or through fastening of frame 36 to balloon 106, as by adhesive, melting, crimping, or any known method. Coatings are then applied to the assembly of frame 36 and balloon 106, in accordance with the above. When balloon 106 is in the desired position within lumen 200, balloon 106 is inflated, wherein the meshed or woven strands 38 of frame 36 coact to distribute the inflation pressure more evenly across the length of balloon 106, as is illustrated in FIG. 14.

Accordingly, it is particularly advantageous to have frame 36 encircle substantially the entire inflated portion of the balloon, however a benefit may obtained for shorter lengths, such as two fifths, one third, or half of the length of the inflated portion of the balloon, particularly where the frame is positioned near the center of the balloon, where the diameter of the balloon would otherwise be the greatest upon inflation.

When it is desired to transfer one or more coatings from the balloon to the lumen wall, frame 36 is disposed beneath the coatings. During inflation of balloon 106, transfer coating 40 is pressed into even engagement with lumen 200, whereby transfer adhesion takes place in a reliable and predictable manner, across the entire width of the coating to be transferred.

The wire frame described is additionally beneficial for promoting a uniform contact pressure for coatings containing substances which must diffuse or elute into the lumen while the balloon is expanded, as well. In this application, an even contact pressure increases the likelihood of consistent dosing throughout the region of desired application. Where it is not desired to transfer a coating, it is possible for the coatings to be applied underneath frame 36, provided that strands 38 are sufficiently thin and spaced apart to allow contact between the coating and the lumen wall.

Frame 36 is fabricated from a biocompatible material, or is coated with a biocompatible material. If frame 36 is intended to resume a smaller diameter in contact with a deflated balloon, wherein it may be removed from the body, it comprises a resilient material. A resilient material includes but is not limited to polymers, polymer coated metals, and shape memory alloys (SMA), including copper-zinc-aluminium-nickel, copper-aluminium-nickel, and nickel-titanium (NiTi) alloys.

In embodiments in accordance with the invention where it is intended for frame 36 to remain in contact with the lumen, a material is selected which will maintain a stretched shape after the balloon is deflated, including a biodegradable polymer, and which will biodegrade after a desired interval, particularly after the therapeutic substance has diffused into the lumen wall. Frame 36 may additionally be coated with a therapeutic substance as described herein, and therefore contribute to diffusion into the lumen wall during inflation contact, and or until biodegradation.

In accordance with a further aspect of the invention, it is advantageous to inflate and deflate the balloon, thereby providing rest periods during which diffusion into the tissue to be treated may take place, and or to provide periods of increased blood flow. It is specifically contemplated that a period of 5 to 60 seconds of inflation is advantageous, optionally followed by a resting period, and then one or more additional inflations of 5 to 60 seconds, or longer as the medical practitioner deems appropriate.

Where depressions or undulations are present, an initial loading of therapeutic substance into the body lumen may be accomplished. A quantity of therapeutic substance may diffuse through the coating, from the reservoirs formed by the depressions or undulations. Maintaining one or more extended inflation periods provides time for this increased quantity of therapeutic substance to diffuse into the body tissues. In cases where a device in accordance with the invention is used within the circulatory system, as in an artery, adequate blood supply must be maintained during periods of extended inflation. This is accomplished through the use of perfusion ports, as is known in the art. Ultimately, where a layer of coating is transferred, a maintenance supply of therapeutic substance remains with the body lumen wall after the catheter, balloon, and frame, if the latter is employed, are removed.

In accordance with another aspect of the invention, the invention is advantageously employed in the treatment of hard plaque or soft plaque.

In another embodiment in accordance with the invention, a plurality of balloons are deployed on a single catheter, thereby increasing the area which may treated within a particular time period.

It should be understood that while a balloon is described herein as a means for expansion, it is specifically contemplated that other expanding members, including mechanical, hydraulic, or other means for expanding a coating towards a lumen wall may be used to carry out the invention.

My U.S. Pat. Nos. 6,517,533, 6,592,548, 6,641,611, and 6,908,480 disclose devices and methods relating to certain aspects of the present invention, and are hereby incorporated by reference in their entirety.

All references cited herein are expressly incorporated by reference in their entirety. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A method for delivering a therapeutic substance to an interior wall of a body lumen, comprising:
    providing a catheter including—
        a catheter lumen,
        a balloon operatively-associated with the catheter,
        a resilient flexible lattice frame encircling a portion of the length of the balloon, and
        a coating applied over at least a portion of the lattice frame and an exterior of the balloon, the coating including a therapeutic substance;
    inflating the balloon with inflation pressure exerted by a gas or liquid passed through the catheter lumen; and
    expanding the lattice frame with the inflated balloon transferring the coating to the interior wall of a body lumen, where the coating will remain after the deflated balloon and lattice are removed together from the body, after which
    the therapeutic substance within the coating diffuses into the body lumen wall.

2. The method of claim 1, wherein the lattice frame encircles more than half of a surface of the balloon.

3. The method of claim 1, wherein the coating comprises at least two layers, including:
    a first layer proximate the balloon, adhered to the balloon; and
    a second layer above the first layer;
    wherein the second layer, when pressed against the body lumen wall, adheres against the body lumen wall and the first layer with greater strength than the strength with which the first layer adheres to the balloon, whereby the first layer is separated from the balloon when the balloon is deflated.

4. The method of claim 1, wherein the coating includes more than one therapeutic substance.

5. The method of claim 1, wherein the coating further includes a contrast agent operative to be readily viewable cooperative with medical imaging apparatus after the catheter, balloon and lattice are removed from the body.

6. The method of claim 1, further comprising perfusion ports within the body of the catheter, operative to permit fluid to flow from the body lumen, through the catheter, and past an inflated balloon.

7. The method of claim 1, wherein the catheter further comprises:
    at least one additional balloon, at least one of which includes at least one of the coating.

8. The method of claim 1, wherein the coating is resilient, and serves to cushion impact of a surface of the balloon with the body lumen wall during inflation, and while the balloon remains inflated.

9. The method of claim 1, wherein inflating the balloon includes inflating the balloon for at least five seconds.

10. The method of claim 1, wherein inflating the balloon is repeated multiple times before removal of the balloon from the body lumen.

11. The method of claim 1, wherein the coating begins diffusion of the therapeutic substance while the balloon is being inflated.

12. A method for delivering a therapeutic substance to an interior wall of a body lumen, comprising:
    providing a catheter including—
        at least one catheter lumen,
        a balloon positioned along the length of the catheter, the balloon inflated through passage of a gas or liquid through at least one of the at least one lumen,
        a resilient flexible lattice frame encircling a portion of the length of the balloon,
        a transfer coating adhered to the lattice with a first adhesion strength, and
        a therapeutic coating adhered to the transfer coating with a second adhesion strength that is relatively weaker than the first adhesion strength, the therapeutic coating including a therapeutic substance,
    inflating the balloon with inflation pressure exerted by a gas or liquid passed through the catheter lumen, the lattice frame expanding together with the inflated balloon, thereby transferring the therapeutic coating to the interior wall of a body lumen; and
    deflating the balloon and lattice and removing the catheter together with the balloon and attached lattice, after which the coating will remain and diffuse the therapeutic substance into the body.

13. The method of claim 12, wherein a portion of the transfer coating remains with the therapeutic coating after the catheter is removed from the body, the transfer coating removed in the body by at least one of dissolving, disintegrating, and biodegrading.

14. The method of claim 12, wherein the transfer coating is lubricious.

15. The method of claim 12, wherein inflating the balloon includes substantially uniformly inflating the balloon along its length, due to a force imparted by the lattice.

16. The method of claim 12, wherein the lattice expands and shrinks together with the balloon.

17. The method of claim 12, wherein the lattice is expanded and shrunk together with the balloon for at least one predetermined interval, before the catheter is removed from the body.

18. The method of claim 17, wherein the lattice and balloon are expanded and shrunk together for a plurality of intervals.

19. A catheter for delivering a therapeutic substance to an interior wall of a body lumen, the catheter comprising:
    a lumen;
    a balloon positioned along the length of the catheter, the balloon inflated through passage of a gas or liquid through at least one of the at least one lumen;
    a resilient flexible lattice frame encircling a portion of the length of the balloon;
    a transfer coating adhered to the lattice with a first adhesion strength;
    a therapeutic coating adhered to the transfer coating with a second adhesion strength that is relatively weaker than the first adhesion strength, the therapeutic coating including a therapeutic substance, the therapeutic coating transferrable to the body lumen upon inflating the balloon with inflation pressure exerted by a gas or liquid passed through the catheter lumen, the lattice frame expanding together with the inflated balloon, the balloon deflatable together with the attached lattice, whereby the balloon and lattice are removable together with the catheter, after which the coating will remain to diffuse the therapeutic substance into the body.

20. The catheter of claim 19, the lattice fabricated from a resilient material selected from the group including a polymer, polymer coated metal, shape memory alloy, a copper-zinc-aluminum-nickel alloy, a copper-aluminum-nickel alloy, and a nickel-titanium alloy.

* * * * *